(12) United States Patent
Dang et al.

(10) Patent No.: US 11,874,211 B2
(45) Date of Patent: Jan. 16, 2024

(54) METHOD AND DEVICE FOR OBTAINING MICROSCOPIC OCCURRENCE CHARACTERISTICS OF OIL STORED IN A SHALE

(71) Applicant: XI'AN SHIYOU UNIVERSITY, Xi'an (CN)

(72) Inventors: Wei Dang, Xi'an (CN); Xiaoliang Wei, Xi'an (CN)

(73) Assignee: Xi'An Shiyou University, Xi'An (CN)

( * ) Notice: Subject to any disclaimer, the term of this patent is extended or adjusted under 35 U.S.C. 154(b) by 0 days.

(21) Appl. No.: 18/050,172

(22) Filed: Oct. 27, 2022

(65) Prior Publication Data

US 2023/0146357 A1 May 11, 2023

(30) Foreign Application Priority Data

Nov. 11, 2021 (CN) .......................... 202111334952.3

(51) Int. Cl.
*G01N 7/04* (2006.01)
*G01N 15/08* (2006.01)
(Continued)

(52) U.S. Cl.
CPC ............. *G01N 15/088* (2013.01); *G01N 7/04* (2013.01); *G01N 33/241* (2013.01); *G06F 30/28* (2020.01); *G01N 2015/0866* (2013.01)

(58) Field of Classification Search
CPC ...... G01N 15/088; G01N 15/08; G01N 15/00; G01N 2015/0866; G01N 33/241;
(Continued)

(56) References Cited

U.S. PATENT DOCUMENTS

| 7,210,342 B1 * | 5/2007 | Sterner | ................... E21B 21/01 |
| | | | 73/152.23 |
| 2003/0178191 A1 * | 9/2003 | Maher | ..................... E21B 43/24 |
| | | | 166/65.1 |

(Continued)

FOREIGN PATENT DOCUMENTS

| CN | 105445442 A | 3/2016 |
| CN | 106547966 A | 3/2017 |

(Continued)

OTHER PUBLICATIONS

Chen, Xiao-hui, "Advances in the Research on the Occurrence State and Resources Assessment of Shale Oil", Science Technology and Engineering, vol. 17, No. 3, Jan. 2017, pp. 136-144.

(Continued)

*Primary Examiner* — Jeffrey P Aiello
(74) *Attorney, Agent, or Firm* — AP3 Law Firm PLLC

(57) ABSTRACT

A method and device for obtaining microscopic occurrence characteristics of oil stored in a shale, where the microscopic occurrence characteristics include the adsorbed oil film thicknesses in the shale and the oil distribution in the shale. The method includes four steps. The first step is an experiment step in which a N-Hexane vapor adsorption experiment is performed on a sample made from a shale. The second step is a first obtaining step for calculating and obtaining the adsorbed oil film thicknesses in the shale. The third step is a first calculating step and the fourth step is a second obtaining step. They aim to obtain the oil distribution in the shale.

3 Claims, 5 Drawing Sheets

(51) Int. Cl.
*G01N 33/24* (2006.01)
*G06F 30/28* (2020.01)

(58) Field of Classification Search
CPC .. G01N 33/2823; G01N 7/04; G01N 30/8693; G01N 1/405; G01N 2030/025; G01N 2030/8854; G06F 30/28; E21B 49/00; E21B 49/08; E21B 49/10; E21B 49/0875; E21B 43/30; E21B 47/00; G01V 11/00; G01V 2210/624; G01V 3/38; G16C 20/30; G16C 20/70
USPC ..... 73/38, 866, 152.28, 152.05, 23.2, 23.22; 324/323; 702/13, 11, 19, 6, 12, 2, 189, 702/188, 27, 23; 703/10, 11, 12, 2, 9
See application file for complete search history.

(56) References Cited

U.S. PATENT DOCUMENTS

| | | | | |
|---|---|---|---|---|
| 2004/0020642 | A1* | 2/2004 | Vinegar | E21B 47/0224 166/245 |
| 2012/0232859 | A1* | 9/2012 | Pomerantz | G06F 30/23 703/2 |
| 2019/0346411 | A1* | 11/2019 | Gianchandani | G01N 30/38 |
| 2021/0333245 | A1* | 10/2021 | Al-Arfaj | B01D 53/12 |

FOREIGN PATENT DOCUMENTS

| | | |
|---|---|---|
| CN | 107907461 A | 4/2018 |
| CN | 108414424 A | 8/2018 |
| CN | 110322094 A | 10/2019 |
| CN | 110424956 A | 11/2019 |
| CN | 111912958 A | 11/2020 |
| CN | 112304837 A | 2/2021 |
| CN | 112304837 B | 6/2021 |
| WO | 2011133885 A1 | 10/2011 |

OTHER PUBLICATIONS

Dang, Wei, et al., "A Systematic Experimental and Modeling Study of Water Adsorption/Desorption Behavior in Organic-Rich Shale with Different Particle Sizes", Chemical Engineering Journal, vol. 426, Jun. 2021, 16 pages.

Dang, Wei, et al., "Methane Adsorption Rate and Diffusion Characteristics in Marine Shale Samples from Yangtze Platform, South China", Energies, vol. 10, Issue 5, May 4, 2017, 23 pages.

Junqian, Li, et al., "Quantitative Evaluation Models of Adsorbed and Free Shale Oil and Its Microscopic Occurrence Mechanism", Oil & Gas Geology, Jun. 2019, pp. 583-592.

Ning, Fang-xing, et al., "An Analysis on Occurrence State and Mobility of Shale Oil in Jiyang Depression", Xinjiang Oil & Gas, vol. 11, No. 3, Sep. 2015, 6 pages.

Wei, Dang, et al., "Thermodynamics and Kinetics of Water Vapor Adsorption Onto Shale: A Case Study of the Permian Shanxi Formation, Ordos Basin", Oil & Gas Geology, Feb. 2021, pp. 173-185.

Zhao, Fajun, et al., "Characteristics and Mechanisms of Solvent Extraction of Heavy Oils from Porous Media", Chemistry and Technology of Fuels and Oils, vol. 51, No. 1, Mar. 2015, pp. 33-40.

* cited by examiner

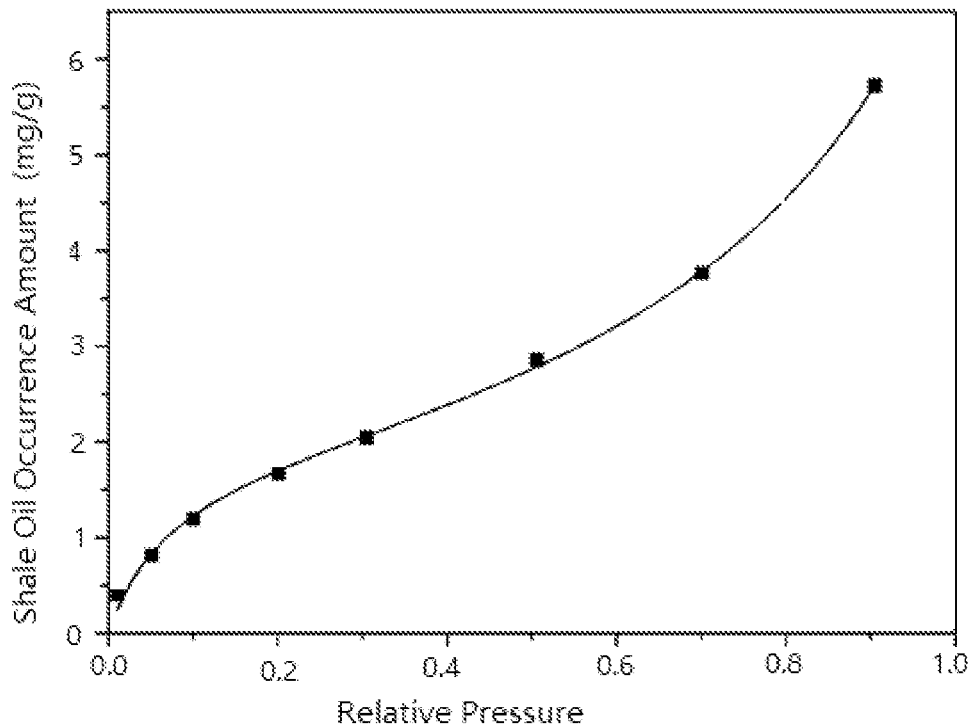

Fig. 2

| | |
|---|---|
| determining a plurality of maximum adsorption amounts of monolayer adsorption of oil in the shale according to the plurality of adsorbed amounts of N-Hexane collected in S101, where the plurality of maximum adsorption amounts of monolayer adsorption of oil corresponds one-to-one to the plurality of adsorbed amounts of N-Hexane | S301 |
| calculating the adsorbed oil film thicknesses in the shale according to the plurality of maximum adsorption amounts of monolayer adsorption of oil determined in S301 and the plurality of adsorbed amounts of N-Hexane collected in S101, where the adsorbed oil film thicknesses in the shale corresponds one-to-one to the plurality of maximum adsorption amounts of monolayer adsorption of oil | S302 |

Fig. 3

METHOD AND DEVICE FOR OBTAINING MICROSCOPIC OCCURRENCE CHARACTERISTICS OF OIL STORED IN A SHALE

CROSS-REFERENCE TO RELATED APPLICATIONS

This application claims priority to Chinese Patent Application No. 202111334952.3, filed on Nov. 11, 2021, which is hereby incorporated herein by reference in its entirety.

TECHNICAL FIELD

The present application relates to the technical field of shale oil geological analysis, and in particular, to a method and device for obtaining microscopic occurrence characteristics of oil stored in a shale.

BACKGROUND

With the continuous development of unconventional oil and gas fields, shale oil has become a global energy hotspot. Quantitative characterization of the occurrence characteristics of shale oil in micropores and nanopores is of great significance for understanding the occurrence mechanism of shale oil, evaluating the oil content and mobility of shale oil, and improving the recovery of shale oil.

In recent years, several methods have been proposed to analyze the mechanisms and characterization of oil storage in shale pores, including Environmental Scanning Electron Microscopy (ESEM), Solvent Extraction combined with Gas Adsorption or Mercury Intrusion (SE-GA/MI), Nuclear Magnetic Resonance (NMR), and Molecular Dynamics Simulation (MDS).

The ESEM allows the direct observation of the pore fluids (such as oil and water) in pore spaces without pre-treatment. The ESEM can obtain the microscopic occurrence information of shale oil, which includes contact relationship, occurrence location, occurrence form, etc. Although this method is simple and convenient without sample pretreatment, it has at least two limitations. The first limitation is of not being able to quantitatively characterize the oil storage. The second limitation is that it can only obtain the microscopic occurrence information of shale oil in the observed part, which is not applicable to the surroundings of the observed part.

The SE-GA/MI method has been used to analyze the oil distribution in shale nanopores. This method uses different types of solvents to extract the oil and then uses nitrogen/carbon dioxide adsorption or mercury intrusion to analyze the change in the pore structure in the shale before and after oil extraction. Information on oil distribution can be derived from this change. The SE-GA/MI method is able to provide quantitative information but is labor-intensive and time consuming. Besides, when a large amount of solvent is used for the extraction, not only the pore structure of shale may be damaged, causing experimental analysis error, but also whether the liquid oil in the nanopores can be successfully extracted cannot be known in advance.

The NMR method uses T2 relaxation time of nuclear magnetic resonance to characterize the occurrence of movable pore fluids in reservoir rocks such as shale and sandstone. Although the experimental process is fast, the preparation of fluid saturated shale samples (e.g., water-saturated and liquid hydrocarbon-saturated) is time-consuming. In addition, the experiment results could be biased by Iron-bearing minerals such as pyrite and siderite in the shale. The iron-bearing minerals generate strong internal magnetic field in shale sample, which seriously reduces the signal to noise ratio of nuclear magnetic resonance signal, thus seriously affecting the accuracy of the experiment results.

The MDS is a theoretical analysis method which reveals the occurrence characteristics of shale oil in pores by simulating the molecular dynamics characteristics of liquid hydrocarbons in shale pores. However, this method is to simplify the underground complex shale oil reservoir into a single liquid hydrocarbon and carbon, or a single mineral, which is quite different from the underground complex shale oil reservoir conditions. The simulation results have not been validated by experimental results and, therefore the accuracy and reliability of this method have not been defined.

In summary, with all the methods described above, the quantitative analysis of the mechanisms and characterization of oil storage in shale pores is still a problem.

SUMMARY

This and other problems are generally solved or circumvented, and technical advantages are generally achieved, by embodiments of the present application which provides a method and device for obtaining microscopic occurrence characteristics of oil stored in a shale.

Technical Problems

The application provides a method and device for obtaining microscopic occurrence characteristics of oil stored in a shale, and intends to solve the technical problem that how to quantitatively analyze the mechanisms and characterization of oil storage in shale pores.

Technical Solutions

The present application provides a method for obtaining microscopic occurrence characteristics of oil stored in a shale, where the microscopic occurrence characteristics include the adsorbed oil film thicknesses in the shale and the oil distribution in the shale. The method includes four steps. The first step is an experiment step in which a N-Hexane vapor adsorption experiment is performed on a sample made from the shale. In the experiment, the N-Hexane vapor is absorbed by the sample under several pressures of N-Hexane vapor. The adsorbed amounts of N-Hexane are collected and they correspond one-to-one to the pressures of N-Hexane vapor. In the present application, N-Hexane is used to simulate shale oil. The amount of N-Hexane adsorbed by the sample is equivalent to the occurrence amount of shale oil in the sample. Actually, the experiment step realizes the reconstruction of shale oil microscopic occurrence of the sample, that is, the sample changes from the state without shale oil to, after the adsorption process, the state of containing N-Hexane which simulates shale oil in its pores. The remaining three steps, based on the experiment data of the first step, obtain shale oil microscopic occurrence characteristic information including the adsorbed oil film thicknesses in the shale and an oil distribution in the shale, which can quantitatively and accurately characterize the microscopic occurrence characteristics of shale oil of the sample, as well as the reservoir rocks within a certain range around the sampling point of the sample, thus realizing quantitatively analyze the mechanisms and characterization of oil storage in shale pores.

The second step is a first obtaining step for calculating and obtaining the adsorbed oil film thicknesses in the shale. The second step, based on the experiment data of the first step, calculates and obtains several adsorbed oil film thicknesses under the several pressures of N-Hexane vapor. Although the adsorbed oil film thicknesses are obtained by taking N-Hexane as the adsorbed material, they are also applicable to the situation where shale oil is adsorbed by shale, and it can characterize the microscopic occurrence characteristics of shale oil within the sample, as well as within a certain range around the sampling point of the sample.

The third step is a first calculating step and the fourth step is a second obtaining step. They aim to obtain the oil distribution in the shale, i.e., the distribution of oil within different sized pores of the shale. Under different pressures, the diameters of the pores that can store shale oil (i.e., valid pore diameters) in shale may be different. In the third step, the present application proposes a relationship between pressure and valid pore diameter, and calculates several valid pore diameters corresponding to different pressures according to the relationship. In the fourth step, based on the experiment data of the first step (i.e., the adsorbed amounts of N-Hexane adsorbed by the sample at different pressures) and the calculation results of the third step (i.e., the valid pore diameters corresponding to different pressures), the relationship between adsorbed amount of N-Hexane (it is equivalent to the occurrence amount of shale oil) and valid pore diameter is obtained. The oil distribution in the shale can be draw from this relationship, i.e., from this relationship, it can be known that which pores (distinguished by diameter value) shale oil is distributed in. The oil distribution obtained in the fourth step, the same as above, can characterize the microscopic occurrence characteristics of shale oil within the sample, as well as within a certain range around the sampling point of the sample.

Advantageous Effects of the Disclosure

Compared with the prior art, advantageous effects of the method provided by the present application are as follows.

Based on the N-Hexane vapor adsorption experiment and the relationship between pressure and valid pore diameter, the adsorbed oil film thicknesses and the oil distribution in the shale can be obtained through the method provided by the present application, thus the microscopic occurrence characteristics of shale oil can be characterized quantitatively and precisely. The analysis process of this method saves time and effort, and the results are accurate.

Compared with the ESEM method in the prior art, this method is able to quantitatively characterize the oil storage, and this method not only can obtain the microscopic occurrence characteristics of shale oil within the sample, but also can obtain those within a certain range around the sampling point of the sample. The fineness of the characterization and the scope of the characterization of this method are greater than the ESEM method.

Compared with the SE-GA/MI method in the prior art, in this method, it is unnecessary to use a large amount of solvent for extraction, which saves time and labor. In addition, it avoids a large number of extractions to damage the pore structure, and the results are more accurate and reliable.

Compared with the NMR method in the prior art, this method does not need to use saturated fluid samples, thus solving the problem of time-consuming preparation of saturated fluid samples. In fact, the adsorbed substance used in this method is N-Hexane, the preparation cost of which is far lower than the saturated fluid sample. In addition, the method provided in the present application has no problem that magnetic substances interfere with the experiment results. Compared with the nuclear magnetic resonance method, the results of this method are more accurate and reliable.

Compared with the MDS method in the prior art, which is a theoretical analysis method, this method obtains shale oil microscopic occurrence characteristic information based on actual experiment, and its results are more accurate and reliable than simulating which simplify the underground complex shale oil reservoir into a single liquid hydrocarbon and carbon, or a single mineral.

BRIEF DESCRIPTION OF THE DRAWINGS

In order to more clearly illustrate the technical solutions in the embodiments of this application, the accompanying drawings to be used in the descriptions of the embodiments or the prior art will be briefly described below. Obviously, the accompanying drawings in the following description are only some embodiments of this application, and for a person of ordinary skill in the art, without involving any inventive effort, other accompanying drawings may also be obtained according to these accompanying drawings.

FIG. 2 is a microscopic occurrence curve of shale oil according to embodiments of the present application;

FIG. 3 is a flow diagram of two steps for calculating and obtaining the adsorbed oil film thicknesses in the shale according to embodiments of the present application;

DETAILED DESCRIPTION OF ILLUSTRATIVE EMBODIMENTS

In order to make the technical problems to be solved by the present application, technical solutions and advantageous effects clearer, the present application will be further described in detail below with reference to the accompanying drawings and embodiments. It should be understood that the specific embodiments described herein are only used to explain the present application, but not to limit the present application.

The method provided by the present application aims to obtain microscopic occurrence characteristics of oil stored in a shale, where the microscopic occurrence characteristics include the adsorbed oil film thicknesses in a shale and the oil distribution in the shale.

Figure 1:
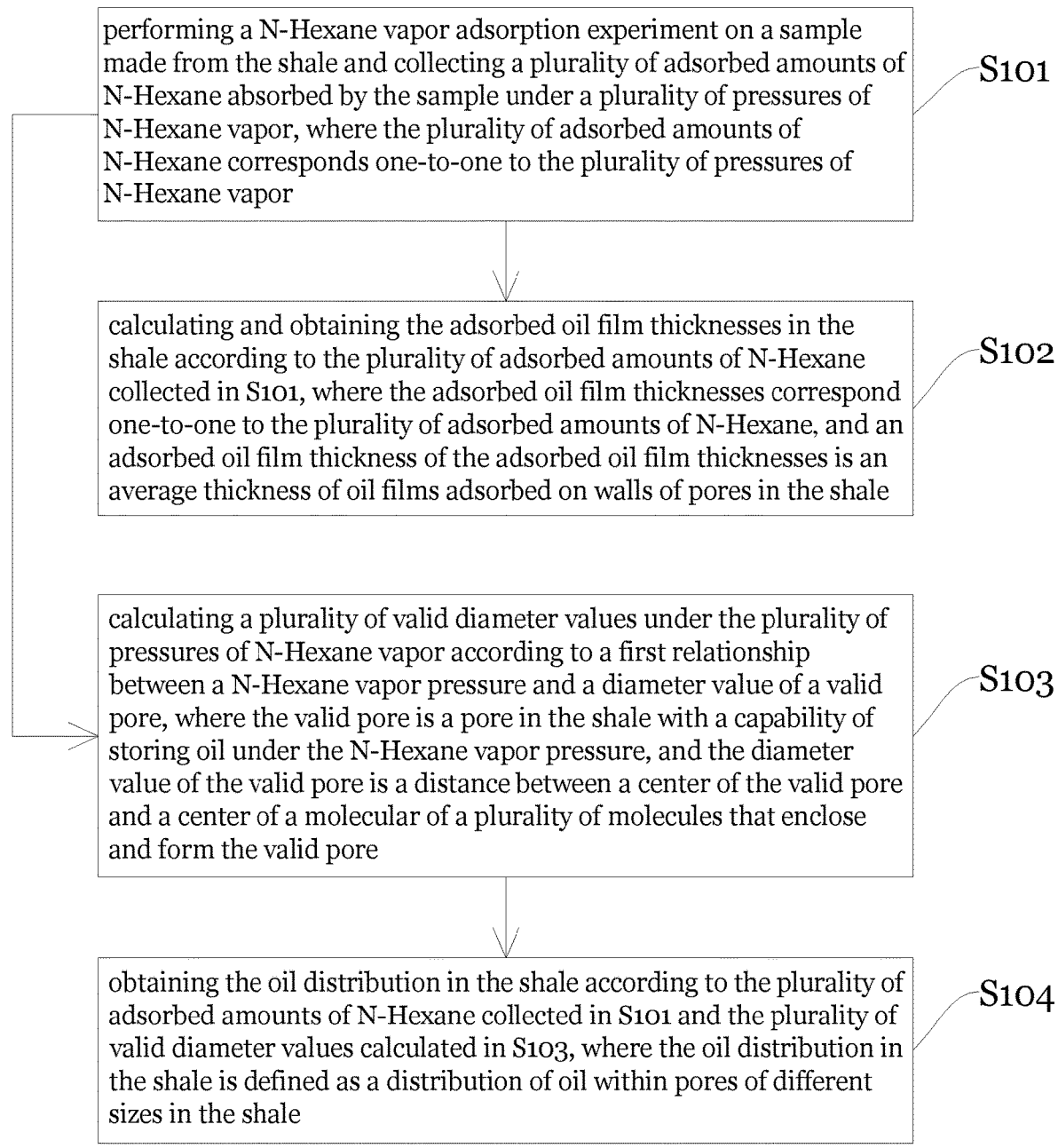
FIG. 1 is a flow diagram of the method for obtaining microscopic occurrence characteristics of oil stored in a shale according to embodiments of the present application.

In one embodiment, the method provided by the present application includes four steps of S101 to S104, as shown in FIG. 1. S101 to S104 are described in detail below.

S101: performing a N-Hexane vapor adsorption experiment on a sample made from the shale and collecting a plurality of adsorbed amounts of N-Hexane absorbed by the sample under a plurality of pressures of N-Hexane vapor, where the plurality of adsorbed amounts of N-Hexane corresponds one-to-one to the plurality of pressures of N-Hexane vapor.

In this step, the N-Hexane vapor adsorption experiment on the sample which is made from the shale. During the experiment, N-Hexane molecules enter the pores of the sample. It is noted that a pore of the sample may be a micropore or a nanopore. The method provided by the present application is suitable for both micropore and nanopore. As the pressure increases, more and more N-Hexane molecules are contained in the pores. Different pressures correspond to different amounts of N-Hexane molecular. The amount of N-Hexane adsorbed by the sample is equivalent to the occurrence amount of shale oil in the sample. Therefore, by S101, it can be obtained that the occurrence amounts of shale oil in the sample under different pressures. The occurrence amounts of shale oil in the sample can further characterize the occurrence amounts of shale oil within the reservoir rocks within a certain range around the sampling point of the sample. It is noted that the pressure in the present application refers to relative pressure. It is known in the art. In S101, the relative pressure is the ratio of the absolute pressure P generated by N-Hexane vapor to the saturated vapor pressure $P_0$ of N-Hexane, i.e., the relative pressure is $P/P_0$. The relative pressure ranges from 0 to 0.99.

Vapor adsorption experiment is experiment means known in the art. However, it should be noted that existing vapor adsorption experiments generally use water, methane, carbon dioxide or nitrogen as adsorbed substances. The present application uses N-Hexane as adsorbed substance, which is different from the prior art. Exemplarily, prior to the adsorption experiment, the shale may be ground into particles to prepare the sample. Soxhlet extraction may be then performed on the particles using a mixed solvent of dichloromethane and methanol to obtain oil-free shale sample, which is prepared for the N-Hexane vapor adsorption experiment. During the adsorption process, N-Hexane molecules enter the pores of the sample particles under the action of vapor pressure to simulate that the sample contains shale oil. The instrument used in the experiment may be a gravimetric vapor adsorption apparatus, which is an equipment in the art. Several isotherms are measured by using the gravimetric apparatus over the relative pressure range from 0 to 0.99. The oil-free shale sample is placed into the sample cell of the gravimetric apparatus. Then, the N-Hexane vapor enters the sample cell and flushes the shale sample at a constant flow rate and temperature. The microbalance is used to measure the amount of vapor adsorbed in the shale sample, as a function of time. After the adsorption equilibrium is reached, the relative pressure is increased to the next target relative pressure step and the subsequent adsorption amount is measured until the equilibrium is reached again. Exemplarily, eight relative pressure steps may be measured to establish the isotherms at temperatures of 308 K, and the equilibrium time for each step was approximately 200-300 min.

In one embodiment, the method provided by the present application includes S101-1: establishing a shale oil microscopic occurrence curve, as shown in FIG. 2, based on the adsorbed amounts of N-Hexane absorbed by the sample under the pressures of N-Hexane vapor collected in S101. In FIG. 2, the abscissa represents the relative pressures and the ordinate represents shale oil occurrence amounts. The microscopic occurrence curve can clearly show the shale oil occurrence amounts under different pressures, and it is also convenient for subsequent analysis and processing.

S102: calculating and obtaining the adsorbed oil film thicknesses in the shale according to the plurality of adsorbed amounts of N-Hexane collected in S101, where the adsorbed oil film thicknesses correspond one-to-one to the plurality of adsorbed amounts of N-Hexane, and an adsorbed oil film thickness of the adsorbed oil film thicknesses is an average thickness of oil films adsorbed on walls of pores in the shale.

The adsorbed oil film thicknesses obtained in this step is able to quantitatively characterize the shale oil microscopic occurrence characteristic.

In one embodiment, referring to FIG. 3, S102 may include S301 and S302.

Figure 8:
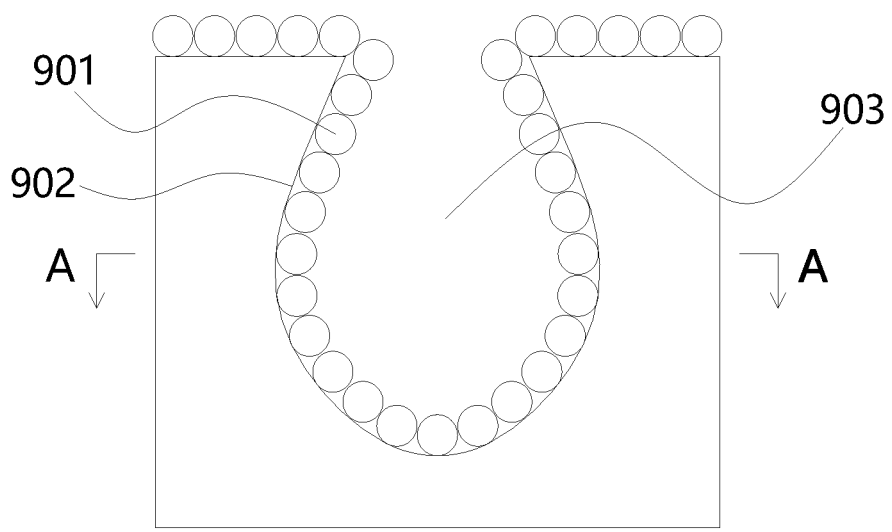
FIG. 8 is a schematic diagram of monolayer adsorption according to embodiments of the present application.

S301: determining a plurality of maximum adsorption amounts of monolayer adsorption of oil in the shale according to the plurality of adsorbed amounts of N-Hexane collected in S101, where the plurality of maximum adsorption amounts of monolayer adsorption of oil corresponds one-to-one to the plurality of adsorbed amounts of N-Hexane. The term "monolayer adsorption" means that, as shown in FIG. 8, one layer of oil molecules 901 attaches to the wall 902 of a pore 903.

In one embodiment, S301 may include S301-1 and S301-2.

S301-1: performing a curve fitting on the plurality of adsorbed amounts of N-Hexane collected in S101 to obtain a microscopic occurrence curve (as shown in FIG. 2) and an analytic expression of the microscopic occurrence curve, where the analytic expression quantitatively describes a second relationship between the N-Hexane vapor pressure, an adsorbed amount of N-Hexane of the plurality of adsorbed amounts of N-Hexane collected in S101 and a maximum adsorption amount of monolayer adsorption of N-Hexane in the sample.

S301-2: determining a plurality of maximum adsorption amounts of monolayer adsorption of N-Hexane in the sample according to the second relationship, the plurality of adsorbed amounts of N-Hexane collected in S101 and the plurality of pressures of N-Hexane vapor.

The plurality of maximum adsorption amounts of monolayer adsorption of N-Hexane in S301-2 is equivalent to the plurality of maximum adsorption amounts of monolayer adsorption of oil in S301. Therefore, the plurality of maximum adsorption amounts of monolayer adsorption of oil is determined.

In one embodiment, the second relationship may be:

$$V_m = \frac{V(1-Ah)(1+Kh-Ah)}{Kh};$$

wherein h is the N-Hexane vapor pressure, V is the adsorbed amount of N-Hexane, $V_m$ is the maximum adsorption amount of monolayer adsorption of N-Hexane, and A and K are two values obtained based on the curve fitting.

The $V_m$, A and K are obtained through fitting the experiment data of S101, i.e., the adsorbed amounts of N-Hexane absorbed by the sample under the pressures of N-Hexane vapor collected in S101. A and K are not involved in subsequent calculations. The order of magnitude of A is about $10^{-1}$ and the order of magnitude of K is about $10^0$ or $10^1$.

$V_m$ in the second relationship is equivalent to the maximum adsorption amount of monolayer adsorption of oil. Therefore, the maximum adsorption amount of monolayer adsorption of oil can be obtained through the second relationship. For example, in one calculation, the maximum adsorption amount of monolayer adsorption of oil is 1.874.

S302: calculating the adsorbed oil film thicknesses in the shale (which is one of the microscopic occurrence characteristics that the present application aims to obtain) according to the plurality of maximum adsorption amounts of monolayer adsorption of oil determined in S301 and the plurality of adsorbed amounts of N-Hexane collected in S101, where the adsorbed oil film thicknesses in the shale corresponds one-to-one to the plurality of maximum adsorption amounts of monolayer adsorption of oil.

In one embodiment, each of the adsorbed oil film thicknesses in the shale is calculated through a third relationship $$t = d_1 \frac{V}{V_m},$$

wherein t is an adsorbed oil film thickness of the adsorbed oil film thicknesses in the shale, $d_1$ is an N-Hexane molecular diameter, V is the adsorbed amount of N-Hexane in the second relationship, and $V_m$ is the maximum adsorption amount of monolayer adsorption of N-Hexane in the second relationship.

Figure 4:
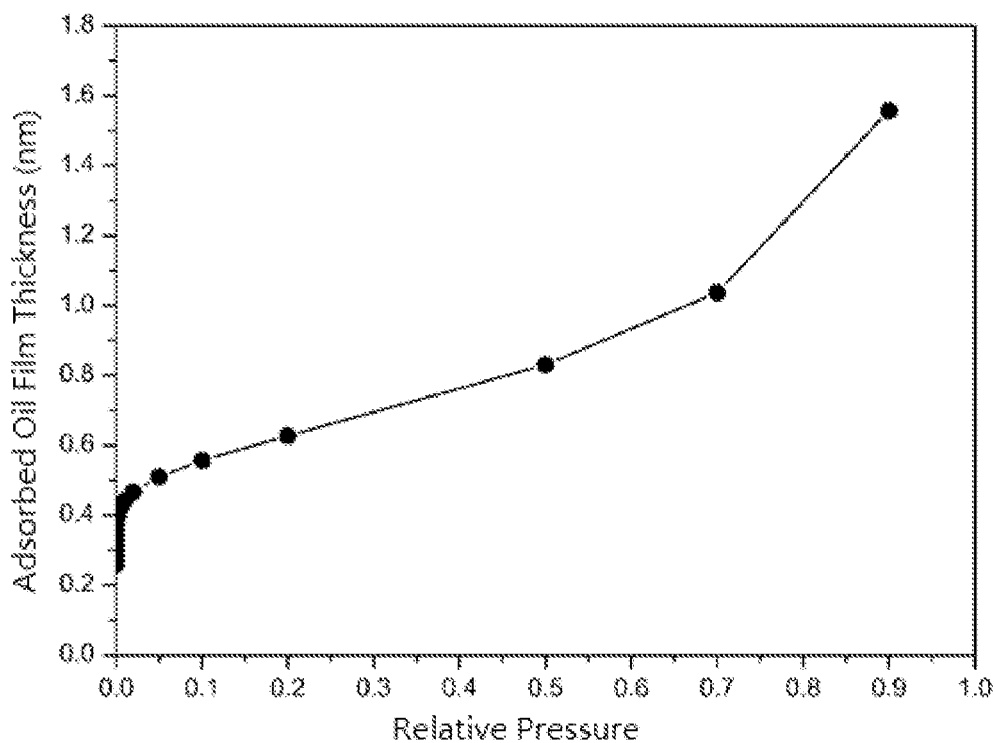
FIG. 4 is a schematic diagram of the adsorbed oil film thicknesses under the relative pressures according to embodiments of the present application.

FIG. 4 is a schematic diagram of the adsorbed oil film thicknesses in the sample under the different pressures of N-Hexane vapor. In FIG. 4, the abscissa represents the relative pressures (i.e., the different pressures of N-Hexane vapor) and the ordinate represents the adsorbed oil film thicknesses.

Figure 9:
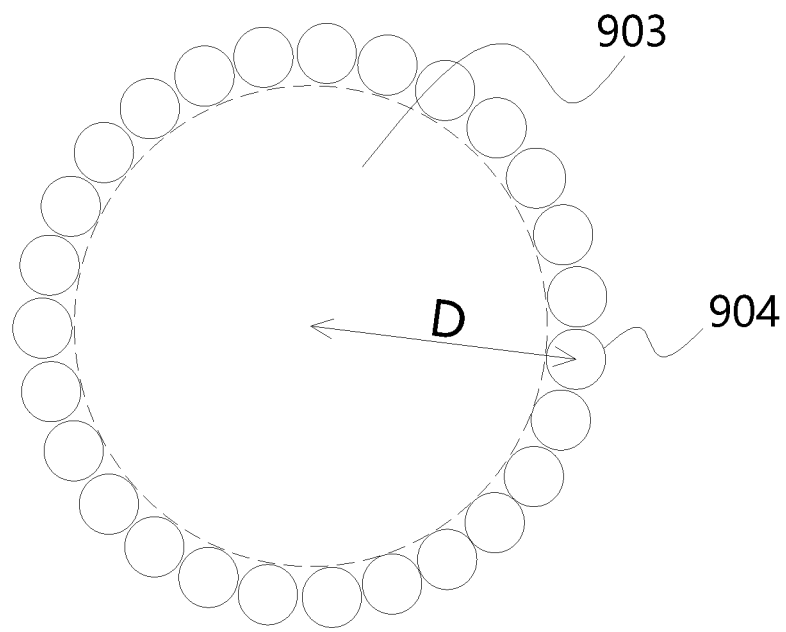
FIG. 9 is a cross-section along the section line A-A according to FIG. 8.

S103: calculating a plurality of valid diameter values under the plurality of pressures of N-Hexane vapor according to a first relationship between a N-Hexane vapor pressure and a diameter value of a valid pore, where the valid pore is a pore in the shale with a capability of storing oil under the N-Hexane vapor pressure, and the diameter value of the valid pore is, as shown in FIG. 9, a distance D between a center of the valid pore 903 and a center of a molecular 904 of a plurality of molecules that enclose and form the valid pore 903.

In S103, the present application proposes (or establishes) the relationship between the pressures and the valid diameter values. In S104, according to the relationship and combining the relationship proposed in S103, the relationship between the valid diameter value and the adsorbed amount of N-Hexane which is equivalent to the occurrence amount of shale oil. It should be noted that although there is a sequence between S103 and S104 (S103 comes first and S104 comes last), the present application does not limit the sequence between S103 and S104 as a whole and S102. That is, S102 may be performed first, then S103 and S104 are performed; or, S103 and S104 may be performed first, then S102 is performed; or, S102 may be performed simultaneously with S103 and S104.

The first relationship proposed in S103 may be obtained based on a known HK model and the physical and chemical properties of N-Hexane. The first relationship quantitatively describes the relationship between relative pressure and valid diameter value.

In one embodiment, the first relationship is $$\ln(h) = \frac{67.51}{2d_2 - 0.77}\left[\frac{3.976 \times 10^{-3}}{(2d_2 - 0.385)^3} - \frac{1.726 \times 10^{-6}}{(2d_2 - 0.385)^9} - 0.06038\right],$$

wherein h is the N-Hexane vapor pressure and $d_2$ is the diameter value of the valid pore. The "ln" in the first relationship is a mathematical symbol representing natural logarithm.

S104: obtaining the oil distribution in the shale according to the plurality of adsorbed amounts of N-Hexane collected in S101 and the plurality of valid diameter values calculated in S103, where the oil distribution in the shale is defined as a distribution of oil within pores of different sizes in the shale.

The distribution of oil within different sized pores in the shale shows a relationship between valid pore diameter and occurrence amount of shale oil. Therefore, when the distribution of oil is known, the occurrence amount of shale oil can be obtained according to the diameters of pores in the shale. This has important guiding significance for the exploration and exploitation of shale oil.

Figure 5:
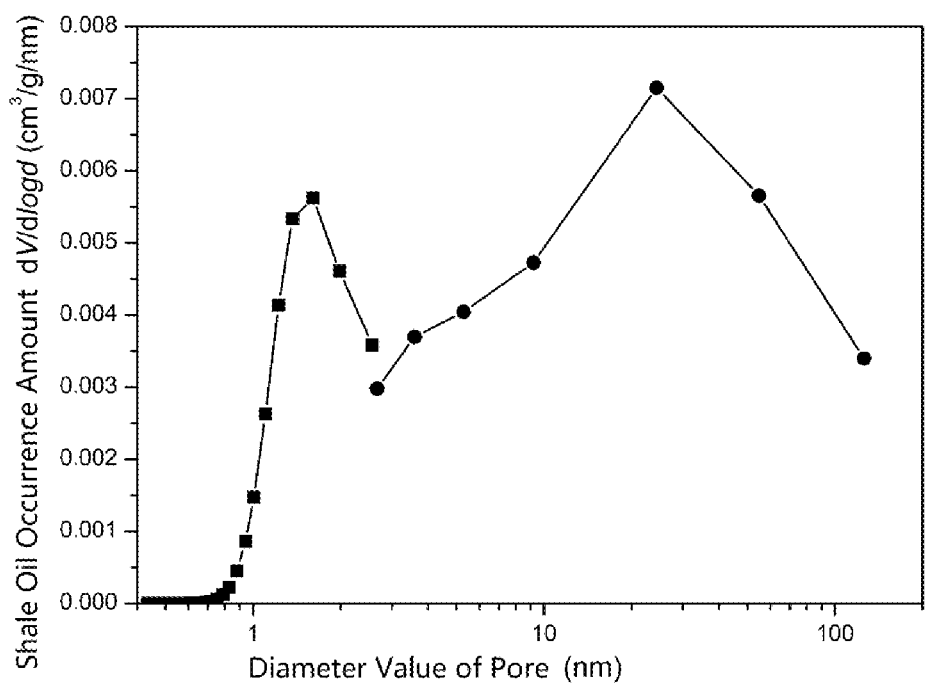
FIG. 5 is a microscopic distribution curve of shale oil according to embodiments of the present application.

In S104, based on the experiment data of S101 (i.e., the adsorbed amounts of N-Hexane adsorbed by the sample at different pressures) and the calculation results of S103 (i.e., the valid pore diameters corresponding to different pressures), the relationship between adsorbed amount of N-Hexane (it is equivalent to the occurrence amount of shale oil) and valid pore diameter is obtained. The oil distribution in the shale can be draw from this relationship, i.e., from this relationship, it can be known that which pores (distinguished by diameter value) shale oil is distributed in. The oil distribution in the shale can be represented by a microscopic distribution curve as shown in FIG. 5. In FIG. 5, the abscissa represents diameter values of pores and the ordinate represents the occurrence amounts of shale oil.

The unit of occurrence amount in FIG. 2 is mg/g. The unit of occurrence amount in FIG. 5 is cm³/g. They are different, but they can transform to each other through the relationship $$\frac{cm^3}{g} = \frac{mg}{g} \times \frac{22.4 \times 0.00598}{87.16}.$$

Through the methods provided by the embodiments of the present application, the adsorbed oil film thicknesses and the oil distribution in the shale can be obtained. Thus, the microscopic occurrence characteristics of shale oil can be characterized quantitatively and precisely. The analysis process of the methods saves time and effort, and the results are accurate. The present application realizes quantitative characterization of occurrence amount of shale oil in different sizes of pores, establishes microscopic distribution curve, clarifies the location and space of shale oil in the pores, and solves the problems of inaccurate characterization results, poor applicability and poor effect of the methods in the prior art. In addition, the methods provided in the present application is not only applicable to shale oil, but also to tight oil. For example, an exploiting of shale oil or tight oil may be performed according to the microscopic occurrence characteristics obtained in the method provided by the present application.

It should be understood that the size of the sequence numbers of the steps in the above description does not mean the sequence of execution, and the execution sequence of each process should be determined by its function and internal logic, and should not constitute any limitation to the implementation process of the present application.

Figure 6:
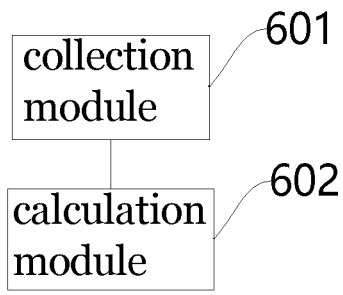
FIG. 6 is a schematic structural diagram of the device or obtaining microscopic occurrence characteristics of oil stored in a shale according to embodiments of the present application.

The present application also provides a device for obtaining microscopic occurrence characteristics of oil stored in a shale, where the microscopic occurrence characteristics includes the adsorbed oil film thicknesses in the shale and the oil distribution in the shale. FIG. 6 is a schematic structural diagram of the device. For the convenience of description, only the parts related to the present application is shown. For details not described in detail therein, reference may be made to the above description of the methods.

As shown in FIG. 6, in one embodiment, the device may include a collection module 601 and a calculation module 602.

The collection module 601 is configured to collect experiment data in a N-Hexane vapor adsorption experiment on a sample made from the shale, where the experiment data includes a plurality of adsorbed amounts of N-Hexane absorbed by the sample under a plurality of pressures of N-Hexane vapor, and the plurality of adsorbed amounts of N-Hexane corresponds one-to-one to the plurality of pressures of N-Hexane vapor.

The calculation module 602 is configured to calculate and obtain the adsorbed oil film thicknesses in the shale according to the plurality of adsorbed amounts of N-Hexane, where the adsorbed oil film thicknesses correspond one-to-one to the plurality of adsorbed amounts of N-Hexane, and an absorbed oil film thickness of the absorbed oil film thicknesses is an average thickness of oil films adsorbed on walls of pores in the shale.

The calculation module 602 is also configured to calculate a plurality of valid diameter values under the plurality of pressures of N-Hexane vapor according to a first relationship between a N-Hexane vapor pressure and a diameter value of a valid pore, where the valid pore is a pore in the shale with a capability of storing oil under the N-Hexane vapor pressure, and the diameter value of the valid pore is a distance between a center of the valid pore and a center of a molecular of a plurality of molecules that enclose and form the valid pore.

The calculation module 602 is also configured to obtain the oil distribution in the shale according to the plurality of adsorbed amounts of N-Hexane and the plurality of valid diameter values, where the oil distribution in the shale is defined as a distribution of oil within pores of different sizes in the shale.

In one embodiment, the calculation module 602 is also configured to:
  determine a plurality of maximum adsorption amounts of monolayer adsorption of oil in the shale according to the plurality of adsorbed amounts of N-Hexane, where the plurality of maximum adsorption amounts of monolayer adsorption of oil corresponds one-to-one to the plurality of adsorbed amounts of N-Hexane; and
  calculate the adsorbed oil film thicknesses in the shale according to the plurality of maximum adsorption amounts of monolayer adsorption of oil and the plurality of adsorbed amounts of N-Hexane, where the adsorbed oil film thicknesses correspond one-to-one to the plurality of maximum adsorption amounts of monolayer adsorption of oil.

In one embodiment, the calculation module 602 is also configured to:
  perform a curve fitting on the plurality of adsorbed amounts of N-Hexane to obtain a microscopic occurrence curve and an analytic expression of the microscopic occurrence curve, where the analytic expression quantitatively describes a second relationship between the N-Hexane vapor pressure, an adsorbed amount of N-Hexane of the plurality of adsorbed amounts of N-Hexane and a maximum adsorption amount of monolayer adsorption of N-Hexane in the sample; and
  determine a plurality of maximum adsorption amount of monolayer adsorption of N-Hexane in the sample according to the second relationship, the plurality of adsorbed amounts of N-Hexane and the plurality of pressures of N-Hexane vapor.

In one embodiment, the second relationship is:

$$V_m = \frac{V(1-Ah)(1+Kh-Ah)}{Kh},$$

where h is the N-Hexane vapor pressure, V is the adsorbed amount of N-Hexane, $V_m$ is the maximum adsorption amount of monolayer adsorption of N-Hexane, and A and K are two values obtained based on the curve fitting.

In one embodiment, each of the adsorbed oil film thicknesses in the shale is calculated through a third relationship $$t = d_1 \frac{V}{V_m},$$

where t is an adsorbed oil film thickness of the adsorbed oil film thicknesses in the shale, $d_1$ is an N-Hexane molecular diameter, V is the adsorbed amounts of N-Hexane in the second relationship, and $V_m$ is the maximum adsorption amount of monolayer adsorption of N-Hexane in the second relationship.

In one embodiment, the first relationship between the N-Hexane vapor pressure and the diameter value of the valid pore is:

$$\ln(h) = \frac{67.51}{2d_2 - 0.77}\left[\frac{3.976 \times 10^{-3}}{(2d_2 - 0.385)^3} - \frac{1.726 \times 10^{-6}}{(2d_2 - 0.385)^9} - 0.06038\right],$$

where h is the N-Hexane vapor pressure and $d_2$ is the diameter value of the valid pore.

The devices provided by the present application is able to perform the methods provided the present application. Therefore, through the devices provided by the embodiments of the present application, the adsorbed oil film thicknesses and the oil distribution in the shale can be obtained. Thus, the microscopic occurrence characteristics of shale oil can be characterized quantitatively and precisely. The analysis process of the methods saves time and effort, and the results are accurate. The present application realizes quantitative characterization of occurrence amount of shale oil in different sizes of pores, establishes microscopic distribution curve, clarifies the location and space of shale oil in the pores, and solves the problems of inaccurate characterization results, poor applicability and poor effect of the methods in the prior art.

Figure 7:
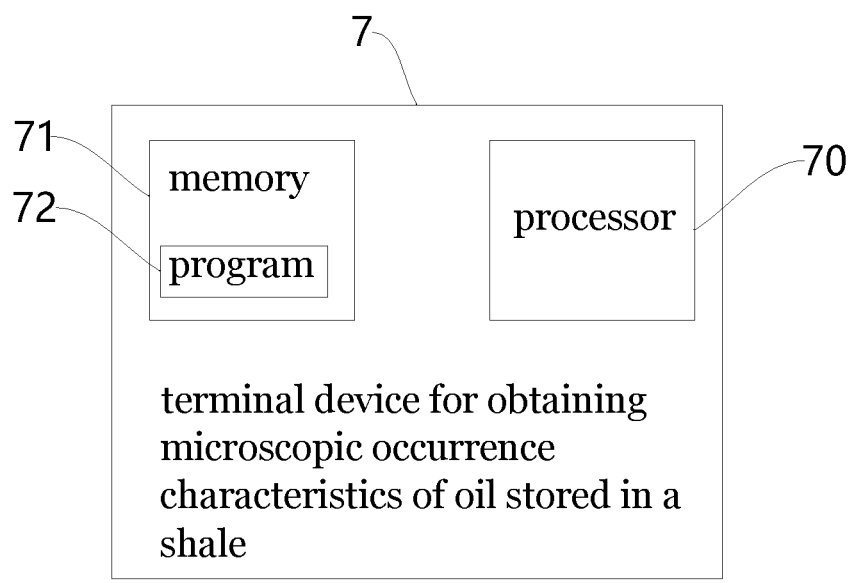
FIG. 7 is a schematic structural diagram of the terminal device or obtaining microscopic occurrence characteristics of oil stored in a shale according to embodiments of the present application.

The present application also provides a terminal device for obtaining microscopic occurrence characteristics of oil stored in a shale. FIG. 7 is a schematic structural diagram of the terminal device. As shown in FIG. 7, the terminal device 7 includes a non-transitory memory 71 storing a computer executable program 72 and a processor 70 to execute the program 72. When the processor 70 executes the program 72, the steps in the above-mentioned embodiments of the method for obtaining microscopic occurrence characteristics of oil stored in a shale, for example, steps S101 to S104 shown in FIG. 1, are implemented. Alternatively, when the processor 70 executes the program 72, the functions of the modules in each of the foregoing device embodiments, such as the functions of the modules 601 and 602 shown in FIG. 6, are implemented.

Exemplarily, the program 72 may be divided into one or more modules/units, and the one or more modules/units are stored in the memory 71 and executed by the processor 70 to implement the present application. The one or more modules/units may be a series of computer program instruction segments capable of performing specific functions, and the instruction segments are used to describe the execution process of the program 72 in the device provided by the present application. For example, the program 72 can be divided into modules 601 and 602 shown in FIG. 6.

The terminal device 7 may be a computing device such as a desktop computer, a notebook, a handheld computer, and a cloud server. The terminal device 7 may include, but is not limited to, a processor 70 and a memory 71. Those skilled in the art can understand that FIG. 7 is only an example of the terminal device 7, and does not constitute a limitation on the terminal device 7. The terminal device 7 may include more or less components than shown, or some components may be combined, or different components, for example, the terminal device 7 may also include input and output devices, network access devices, buses, and the like.

The processor 70 may be a central processing unit (CPU), and may also be other general-purpose processors, digital signal processors (DSP), application specific integrated circuits (ASIC), Field-Programmable Gate Array (FPGA) or other programmable logic devices, discrete gate or transistor logic devices, discrete hardware components, etc. The general-purpose processor may be a microprocessor or any conventional processor or the like.

The memory 71 may be an internal storage unit of the terminal device 7, such as a hard disk or a memory of the terminal device 7. The memory 71 may also be an external storage device of the terminal device 7, such as a plug-in hard disk, a smart memory card (SMC), a secure digital card (SD) equipped on the terminal device 7, flash card, etc. Further, the memory 71 may also include both an internal storage unit of the terminal device 7 and an external storage device. The memory 71 is used to store the computer program and other programs and data required by the control device. The memory 71 can also be used to temporarily store data that has been output or will be output.

Those skilled in the art can clearly understand that, for the convenience and brevity of description, only the division of the above-mentioned functional units and modules is used as an example for illustration. In practical applications, the above-mentioned function allocation can be completed by different functional units and modules as required, that is, the internal structure of the device is divided into different functional units or modules to complete all or part of the functions described above. Each functional unit and module in the embodiments may be integrated into one processing unit, or each unit may exist physically alone, or two or more units may be integrated into one unit. The above-mentioned integrated units may be implemented in the form of hardware, or may be implemented in the form of software functional units. In addition, the specific names of the functional units and modules are only for the convenience of distinguishing from each other, and are not used to limit the protection scope of the present application. For the specific working process of the units and modules in the above-mentioned device, reference may be made to the corresponding process in the foregoing method embodiments, which will not be repeated here.

In the above-mentioned embodiments, the description of each embodiment has its own emphasis. For parts that are not described or described in detail in a certain embodiment, reference may be made to the relevant descriptions of other embodiments.

Those of ordinary skill in the art can realize that the units and algorithm steps of each example described in conjunction with the embodiments disclosed herein can be implemented in electronic hardware, or a combination of computer software and electronic hardware. Whether these functions are performed in hardware or software depends on the specific application and design constraints of the technical solution. Skilled artisans may implement the described functionality using different methods for each particular application, but such implementations should not be considered beyond the scope of this application.

In the embodiments provided in this application, it should be understood that the disclosed devices and methods may be implemented in other manners. For example, the device embodiments described above are merely illustrative. For example, the division of the modules or units is only a logical function division, and there may be other division methods in actual implementation. For example, multiple units or components may be combined or may be integrated into another system, or some features may be omitted, or not implemented.

The units described as separate parts may or may not be physically separate. A component shown as a unit may or may not be a physical unit, it may be located in one place, or it may be distributed over a number of network elements. Some or all of the units may be selected according to actual needs to achieve the purpose of the solution in this embodiment.

In addition, each functional unit in each embodiment of the present application may be integrated into one processing unit, or each unit may exist physically alone, or two or more units may be integrated into one unit. The above-mentioned integrated units may be implemented in the form of hardware, or may be implemented in the form of software functional units.

The integrated modules/units, if implemented in the form of software functional units and sold or used as independent products, may be stored in a computer-readable storage medium. Based on this understanding, the present application can implement all or part of the processes in the methods of the above embodiments, and can also be completed by instructing relevant hardware through a computer program. The computer program can be stored in a computer-readable storage medium, and when executed by the processor, the computer program can implement the steps of the above-mentioned embodiments of the method for calibrating crosstalk errors in a system for measuring on-wafer S parameters. Where, the computer program includes computer program code, and the computer program code may be in the form of source code, object code, executable file or some intermediate form, and the like. The computer-readable medium may include: any entity or device capable of carrying the computer program code, a recording medium, a U disk, a removable hard disk, a magnetic disk, an optical disk, a computer memory, a read-only memory (ROM), Random Access Memory (RAM), electric carrier signal, telecommunication signal and software distribution medium, etc. It should be noted that the content contained in the computer-readable media may be appropriately increased or decreased according to the requirements of legislation and patent practice in the jurisdiction, for example, in some jurisdictions, according to legislation and patent practice, the computer-readable media Excluded are electrical carrier signals and telecommunication signals.

The above-mentioned embodiments are only used to illustrate the technical solutions of the present application, but not to limit them. Although the present application has been described in detail with reference to the above-mentioned embodiments, those of ordinary skill in the art should understand that the technical solutions described in the foregoing embodiments can still be modified, or some technical features thereof can be equivalently replaced. However, these modifications or replacements do not make the essence of the corresponding technical solutions deviate from the spirit and scope of the technical solutions of the embodiments of the present application, and should be included within the protection scope of the present application.

The invention claimed is:

1. A method comprising:
a first step: performing a N-Hexane vapor adsorption experiment on a sample made from a shale and collecting a plurality of adsorbed amounts of N-Hexane absorbed by the sample under a plurality of pressures of N-Hexane vapor, wherein the plurality of adsorbed amounts of N-Hexane corresponds one-to-one to the plurality of pressures of N-Hexane vapor;
a second step: performing a curve fitting on the plurality of adsorbed amounts of N-Hexane collected in the first step to obtain a microscopic occurrence curve and an analytic expression of the microscopic occurrence curve, wherein the analytic expression quantitatively describes a first relationship that is $$V_m = \frac{V(1-Ah)(1+Kh-Ah)}{Kh},$$

wherein h is an N-Hexane vapor pressure, V is an adsorbed amount of N-Hexane of the plurality of adsorbed amounts of N-Hexane collected in the first step, $V_m$ is a maximum adsorption amount of monolayer adsorption of N-Hexane in the sample, and A and K are two values obtained based on the curve fitting;
a third step: determining a plurality of maximum adsorption amounts of monolayer adsorption of N-Hexane in the sample according to the first relationship, the plurality of adsorbed amounts of N-Hexane collected in the first step and the plurality of pressures of N-Hexane vapor, wherein the plurality of maximum adsorption amounts of monolayer adsorption of N-Hexane corresponds to a plurality of maximum adsorption amounts of monolayer adsorption of oil in the shale, and the plurality of maximum adsorption amounts of monolayer adsorption of oil corresponds one-to-one to the plurality of adsorbed amounts of N-Hexane;
a fourth step: calculating a plurality of adsorbed oil film thicknesses in the shale according to the plurality of maximum adsorption amounts of monolayer adsorption of oil in the third step and the plurality of adsorbed amounts of N-Hexane collected in the first step, wherein the plurality of adsorbed oil film thicknesses corresponds one-to-one to the plurality of maximum adsorption amounts of monolayer adsorption of oil, the plurality of adsorbed oil film thicknesses corresponds one-to-one to the plurality of adsorbed amounts of N-Hexane, an adsorbed oil film thickness of the plurality of adsorbed oil film thicknesses being an average thickness of oil films adsorbed on walls of pores in the shale, and each of the plurality of adsorbed oil film thicknesses in the shale is calculated through a second relationship $$t = d_1 \frac{V}{V_m},$$

wherein t is an adsorbed oil film thickness of the plurality of adsorbed oil film thicknesses in the shale, $d_1$ is an N-Hexane molecular diameter, V is the adsorbed amount of N-Hexane in the first relationship, and $V_m$ is the maximum adsorption amount of monolayer adsorption of N-Hexane in the first relationship;
a fifth step: calculating a plurality of valid diameter values under the plurality of pressures of N-Hexane vapor according to a third relationship between the N-Hexane vapor pressure in the first relationship and a diameter value of a valid pore, wherein the valid pore is a pore in the shale with a capability of storing oil under the N-Hexane vapor pressure, the diameter value of the valid pore is a distance between a center of the valid pore and a center of a molecular of a plurality of molecules that enclose and form the valid pore, and the third relationship is:

$$\ln(h) = \frac{67.51}{2d_2 - 0.77}\left[\frac{3.976 \times 10^{-3}}{(2d_2 - 0.385)^3} - \frac{1.726 \times 10^{-6}}{(2d_2 - 0.385)^9} - 0.06038\right],$$

wherein "ln" represents natural logarithm, his the N-Hexane vapor pressure and $d_2$ is the diameter value of the valid pore;
a sixth step: obtaining an oil distribution in the shale according to the plurality of adsorbed amounts of N-Hexane collected in the first step and the plurality of valid diameter values calculated in the fifth step, the oil distribution in the shale being a distribution of oil within pores of different sizes in the shale; and
a seventh step: performing an exploiting of shale oil or tight oil according to the plurality of adsorbed oil film thicknesses and the oil distribution in the shale.

2. A device comprising:
a non-transitory memory storage comprising instructions; and
one or more processors in communication with the memory storage, wherein the instructions, when executed by the one or more processors, cause the device to:
collect experiment data in a N-Hexane vapor adsorption experiment on a sample made from a shale, wherein the experiment data comprises a plurality of adsorbed amounts of N-Hexane absorbed by the sample under a plurality of pressures of N-Hexane vapor, and the plurality of adsorbed amounts of N-Hexane corresponds one-to-one to the plurality of pressures of N-Hexane vapor;
perform a curve fitting on the plurality of adsorbed amounts of N-Hexane to obtain a microscopic occurrence curve and an analytic expression of the microscopic occurrence curve, wherein the analytic expression quantitatively describes a first relationship that is $$V_m = \frac{V(1-Ah)(1+Kh-Ah)}{Kh},$$

wherein h is an N-Hexane vapor pressure, V is an adsorbed amount of N-Hexane of the plurality of adsorbed amounts of N-Hexane, $V_m$ is a maximum adsorption amount of monolayer adsorption of N-Hexane in the sample, and A and K are two values obtained based on the curve fitting;

determine a plurality of maximum adsorption amount of monolayer adsorption of N-Hexane in the sample according to the first relationship, the plurality of adsorbed amounts of N-Hexane and the plurality of pressures of N-Hexane vapor, wherein the plurality of maximum adsorption amounts of monolayer adsorption of N-Hexane corresponds to a plurality of maximum adsorption amounts of monolayer adsorption of oil in the shale, and the plurality of maximum adsorption amounts of monolayer adsorption of oil corresponds one-to-one to the plurality of adsorbed amounts of N-Hexane;

calculate a plurality of adsorbed oil film thicknesses in the shale according to the plurality of maximum adsorption amounts of monolayer adsorption of oil and the plurality of adsorbed amounts of N-Hexane, wherein the plurality of adsorbed oil film thicknesses corresponds one-to-one to the plurality of maximum adsorption amounts of monolayer adsorption of oil, the plurality of adsorbed oil film thicknesses corresponds one-to-one to the plurality of adsorbed amounts of N-Hexane, an absorbed oil film thickness of the plurality of absorbed oil film thicknesses being an average thickness of oil films adsorbed on walls of pores in the shale, and each of the plurality of adsorbed oil film thicknesses in the shale is calculated through a second relationship $$t = d_1 \frac{V}{V_m},$$

wherein t is an adsorbed oil film thickness of the plurality of adsorbed oil film thicknesses in the shale, $d_1$ is an N-Hexane molecular diameter, V is the adsorbed amount of N-Hexane in the first relationship, and $V_m$ is the maximum adsorption amount of monolayer adsorption of N-Hexane in the first relationship;

calculate a plurality of valid diameter values under the plurality of pressures of N-Hexane vapor according to a third relationship between the N-Hexane vapor pressure in the first relationship and a diameter value of a valid pore, wherein the valid pore is a pore in the shale with a capability of storing oil under the N-Hexane vapor pressure, the diameter value of the valid pore is a distance between a center of the valid pore and a center of a molecular of a plurality of molecules that enclose and form the valid pore, and the third relationship is:

$$\ln(h) = \frac{67.51}{2d_2 - 0.77}\left[\frac{3.976\times10^{-3}}{(2d_2-0.385)^3} - \frac{1.726\times10^{-6}}{(2d_2-0.385)^9} - 0.06038\right],$$

wherein "ln" represents natural logarithm, his the N-Hexane vapor pressure and $d_2$ is the diameter value of the valid pore;

obtain an oil distribution in the shale according to the plurality of adsorbed amounts of N-Hexane and the plurality of valid diameter values, the oil distribution in the shale being a distribution of oil within pores of different sizes in the shale; and perform an exploiting of shale oil or tight oil according to the plurality of adsorbed oil film thicknesses and the oil distribution in the shale.

3. A non-transitory computer readable storage medium storing a computer executable program, wherein when the computer executable program is executed by a processor, a method is performed, and the method comprises:

a first step: performing a N-Hexane vapor adsorption experiment on a sample made from a shale and collecting a plurality of adsorbed amounts of N-Hexane absorbed by the sample under a plurality of pressures of N-Hexane vapor, wherein the plurality of adsorbed amounts of N-Hexane corresponds one-to-one to the plurality of pressures of N-Hexane vapor;

a second step: performing a curve fitting on the plurality of adsorbed amounts of N-Hexane collected in the first step to obtain a microscopic occurrence curve and an analytic expression of the microscopic occurrence curve, wherein the analytic expression quantitatively describes a first relationship that is $$V_m = \frac{V(1-Ah)(1+Kh-Ah)}{Kh},$$

wherein h is an N-Hexane vapor pressure, V is an adsorbed amount of N-Hexane of the plurality of adsorbed amounts of N-Hexane collected in the first step, $V_m$ is a maximum adsorption amount of monolayer adsorption of N-Hexane in the sample, and A and K are two values obtained based on the curve fitting;

a third step: determining a plurality of maximum adsorption amounts of monolayer adsorption of N-Hexane in the sample according to the first relationship, the plurality of adsorbed amounts of N-Hexane collected in the first step and the plurality of pressures of N-Hexane vapor, wherein the plurality of maximum adsorption amounts of monolayer adsorption of N-Hexane corresponds to a plurality of maximum adsorption amounts of monolayer adsorption of oil in the shale, and the plurality of maximum adsorption amounts of monolayer adsorption of oil corresponds one-to-one to the plurality of adsorbed amounts of N-Hexane;

a fourth step: calculating a plurality of adsorbed oil film thicknesses in the shale according to the plurality of maximum adsorption amounts of monolayer adsorption of oil in the third step and the plurality of adsorbed amounts of N-Hexane collected in the first step, wherein the plurality of adsorbed oil film thicknesses corresponds one-to-one to the plurality of maximum adsorption amounts of monolayer adsorption of oil, the plurality of adsorbed oil film thicknesses corresponds one-to-one to the plurality of adsorbed amounts of N-Hexane, an adsorbed oil film thickness of the plurality of adsorbed oil film thicknesses being an average thickness of oil films adsorbed on walls of pores in the shale, and each of the plurality of adsorbed oil film thicknesses in the shale is calculated through a second relationship $$t = d_1 \frac{V}{V_m},$$

wherein t is an adsorbed oil film thickness of the plurality of adsorbed oil film thicknesses in the shale, $d_1$ is an N-Hexane molecular diameter, V is the adsorbed amount of N-Hexane in the first relationship, and $V_m$ is the maximum adsorption amount of monolayer adsorption of N-Hexane in the first relationship;

a fifth step: calculating a plurality of valid diameter values under the plurality of pressures of N-Hexane vapor according to a third relationship between the N-Hexane vapor pressure and a diameter value of a valid pore, wherein the valid pore is a pore in the shale with a capability of storing oil under the N-Hexane vapor pressure, the diameter value of the valid pore is a distance between a center of the valid pore and a center of a molecular of a plurality of molecules that enclose and form the valid pore, and the third relationship is:

$$\ln(h) = \frac{67.51}{2d_2 - 0.77}\left[\frac{3.976 \times 10^{-3}}{(2d_2 - 0.385)^3} - \frac{1.726 \times 10^{-6}}{(2d_2 - 0.385)^9} - 0.06038\right],$$

wherein "ln" represents natural logarithm, h is the N-Hexane vapor pressure and $d_2$ is the diameter value of the valid pore;

a sixth step: obtaining an oil distribution in the shale according to the plurality of adsorbed amounts of N-Hexane collected in the first step and the plurality of valid diameter values calculated in the fifth step, the oil distribution in the shale being a distribution of oil within pores of different sizes in the shale; and a seventh step: performing an exploiting of shale oil or tight oil according to the plurality of adsorbed oil film thicknesses and the oil distribution in the shale.

\* \* \* \* \*